(12) United States Patent
Kimura et al.

(10) Patent No.: US 7,437,907 B2
(45) Date of Patent: Oct. 21, 2008

(54) SENSOR FOR DETECTING SUBSTANCE IN LIQUID AND APPARATUS FOR DETECTING SUBSTANCE IN LIQUID USING THE SAME

(75) Inventors: Tetsuya Kimura, Omihachiman (JP); Koji Fujimoto, Otsu (JP); Kenjiro Okaguchi, Moriyama (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 0 days.

(21) Appl. No.: 11/683,021

(22) Filed: Mar. 7, 2007

(65) Prior Publication Data

US 2007/0154349 A1    Jul. 5, 2007

Related U.S. Application Data

(63) Continuation of application No. PCT/JP2005/012851, filed on Jul. 12, 2005.

(30) Foreign Application Priority Data

Sep. 10, 2004    (JP)    ............................. 2004-263951

(51) Int. Cl.
   *G01N 29/036*   (2006.01)
   *H01L 41/08*    (2006.01)

(52) U.S. Cl. ................. 73/24.06; 73/24.01; 73/61.75; 73/64.53; 310/313 D; 310/313 B; 310/313 R

(58) Field of Classification Search ............... 73/24.01, 73/24.06, 61.75, 64.53; 310/313 R, 313 B, 310/313 D See application file for complete search history.

(56) References Cited

U.S. PATENT DOCUMENTS

| | | | | |
|---|---|---|---|---|
| 4,312,228 A | * | 1/1982 | Wohltjen | 73/597 |
| 4,378,168 A | * | 3/1983 | Kuisma et al. | 374/28 |
| 4,735,906 A | * | 4/1988 | Bastiaans | 436/527 |
| 4,895,017 A | * | 1/1990 | Pyke et al. | 73/24.06 |
| 5,076,094 A | * | 12/1991 | Frye et al. | 73/19.03 |
| 5,283,037 A | * | 2/1994 | Baer et al. | 422/82.01 |

(Continued)

FOREIGN PATENT DOCUMENTS

JP    63-250560 A    10/1988

(Continued)

OTHER PUBLICATIONS

Official Communication for PCT Application No. PCT/JP2005/012851; mailed on Nov. 1, 2005.

(Continued)

*Primary Examiner*—Hezron E. Williams
*Assistant Examiner*—Rose M Miller
(74) *Attorney, Agent, or Firm*—Keating & Bennett, LLP

(57) ABSTRACT

In a sensor for detecting a substance in liquid, recesses are provided in the upper surface of a base substrate. The recesses respectively accommodate SAW elements. A resin layer having openings is arranged such that the sensing portions at the upper surfaces of the SAW elements are exposed in the openings. A reaction film made of a material capable of binding to a target substance is also arranged so as to cover the sensing portion of at least one of the SAW elements. A liquid containing a target substance is fed from the openings.

8 Claims, 11 Drawing Sheets

U.S. PATENT DOCUMENTS

| | | | |
|---|---|---|---|
| 6,543,274 B1 | 4/2003 | Herrmann et al. | |
| 6,626,026 B2 * | 9/2003 | Banda et al. | 73/24.01 |
| 7,170,213 B2 | 1/2007 | Yamanaka et al. | |
| 2007/0145862 A1 * | 6/2007 | Kimura et al. | 310/340 |

FOREIGN PATENT DOCUMENTS

| | | |
|---|---|---|
| JP | 02-238357 A | 9/1990 |
| JP | 05-045338 A | 2/1993 |
| JP | 05-045339 A | 2/1993 |
| JP | 06-194346 A | 7/1994 |
| JP | 09-243618 A | 9/1997 |
| JP | 10-090270 A | 4/1998 |
| JP | 2002-283293 A | 10/2002 |
| JP | 2003-502616 A | 1/2003 |
| JP | 2003-115744 A | 4/2003 |
| JP | 2003-139746 A | 5/2003 |
| JP | 2003-294713 A | 10/2003 |
| JP | 2004-045358 A | 2/2004 |

OTHER PUBLICATIONS

Official communication issued in the counterpart Japanese Application No. 2006-535060, mailed on Mar. 6, 2007.

Nomura et al., "Liquid Sensor Using 2-port Surface Acoustic Wave Resonator," The Institute of Electronics, Information and Communication Engineers, pp. 25-30, (Sep. 2001).

Official communication issued in counterpart Taiwanese Application No. 094127114, dated Jul. 4, 2008.

* cited by examiner

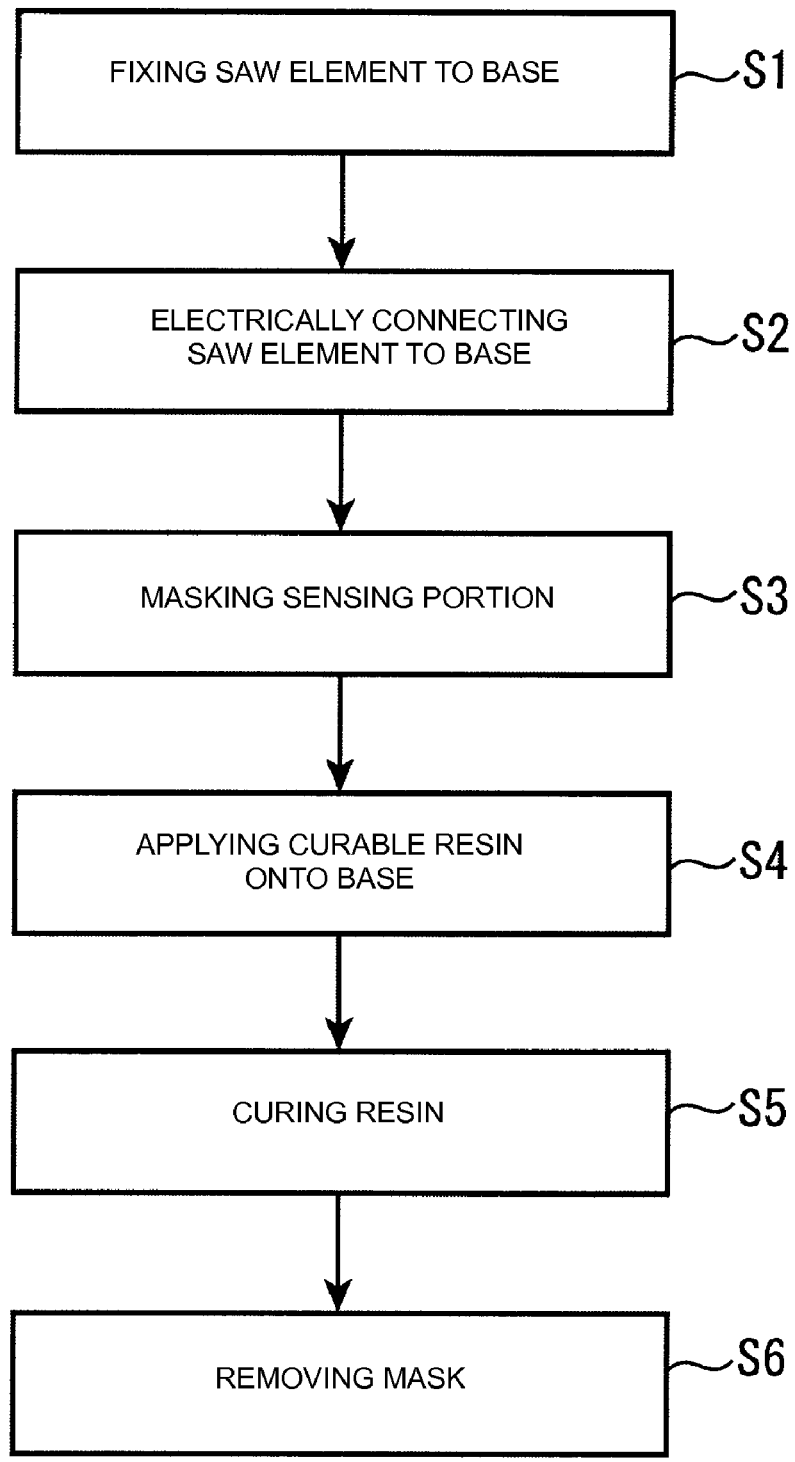

SENSOR FOR DETECTING SUBSTANCE IN LIQUID AND APPARATUS FOR DETECTING SUBSTANCE IN LIQUID USING THE SAME

BACKGROUND OF THE INVENTION

1. Field of the Invention

The present invention relates to sensors for detecting a substance in liquid using a surface acoustic wave element (SAW element) and to apparatuses for detecting a substance in liquid including the sensor. More specifically, the present invention relates to a sensor for detecting a substance in liquid that has a reaction film covering the sensing portion of the SAW element and capable of binding a target substance, and to an apparatus for detecting the substance in liquid including the sensor.

2. Description of the Related Art

Various types of sensors have been proposed for detecting substances in liquid.

For example, Japanese Unexamined Patent Application Publication No. 63-250560 (Patent Document 1) discloses a sensor using surface acoustic waves for a substance in liquid. FIG. 16 is a schematic front sectional view of an in-liquid substance detection sensor disclosed in Patent Document 1.

In FIG. 16, the in-liquid substance detection sensor 102 is immersed in liquid 101 including a target substance. The in-liquid substance detection sensor 102 includes a surface acoustic wave element. More specifically, the in-liquid substance detection sensor 102 includes a rectangular piezoelectric substrate 103, and an input IDT electrode 104 and an output IDT electrode 105 that are disposed on a surface of the piezoelectric substrate 103 with a predetermined distance therebetween. A film 106 for adsorbing a substance to be measured is disposed between the input IDT electrode 104 and the output IDT electrode 105. By applying an alternating voltage to the input IDT electrode 104, surface acoustic waves are excited on the piezoelectric substrate 103. The surface acoustic waves propagate toward the output IDT electrode 105. The output IDT electrode 105 receives a signal according the propagated surface waves and the signal is extracted through the output IDT electrode 105. If the target substance is present, the film 106 adsorbs the target substance, and accordingly, the load of the film 106 on the surface of the piezoelectric substrate 103 varies. Consequently, the propagating surface acoustic waves are changed so that the output extracted from the output IDT electrode 105 is changed due to the presence of the target substance. Thus, the presence or absence and/or the concentration of the target substance can be detected.

However, for the measurement using the in-liquid substance detection sensor 102, the in-liquid substance detection sensor 102 must be immersed in a liquid 101. Accordingly, if the amount of liquid 101 to be measured is small, it is difficult to detect the target substance in the liquid.

If a large amount of liquid is prepared, measuring costs may be increased if the liquid is expensive.

In addition, in the in-liquid substance detection sensor 102, the liquid 101 comes into contact with regions other than the region where surface acoustic waves propagate, that is, the region including electrode pads and bonding wires connected to the IDT electrodes 104 and 105. Therefore, the electrical characteristics can be degraded to undesirably reduce the detection accuracy.

Japanese Unexamined Patent Application Publication No. 5-45339 (Patent Document 2) discloses a method for measuring a detection target substance in a liquid without immersing an in-liquid substance detection sensor including a surface acoustic wave filter in the liquid containing the target substance.

In Patent Document 2, an IDT electrode is provided on a first main surface of the piezoelectric substrate, and a measurement cell for placing the liquid containing the target substance is provided in a second main surface opposite the first main surface. Measurement is performed by placing a liquid in the measurement cell in the second main surface. It is therefore not necessary to immerse the entire in-liquid substance detection sensor in the liquid. In addition, since the liquid does not come into contact with the IDT electrode, the electrical characteristics do not substantially change.

The in-liquid substance detection sensor disclosed in Patent Document 2 does not require a large amount of liquid, or allow liquid to come into contact with the IDT electrode.

In the in-liquid substance detection sensor of Patent Document 2, while the liquid containing the target substance is present in the second main surface of the piezoelectric substrate, the surface acoustic waves propagate very close to the first main surface of the piezoelectric substrate, on which the IDT electrode is provided. The propagation of surface acoustic waves does not accurately respond to whether the liquid is present or absent even if the liquid is present in the second main surface. Accordingly, it is difficult to increase the detection accuracy of the in-liquid substance detection sensor of Patent Document 2.

In addition, the in-liquid substance detection sensor disclosed in Patent Document 2 has another disadvantage in that the leakage component of SH waves, which propagates not only along the surface of the piezoelectric substrate, but also at a certain depth from the surface while dispersing the energy, causes noise which reduces the measurement accuracy.

SUMMARY OF THE INVENTION

To overcome the problems described above, preferred embodiments of the present invention provide a sensor and an apparatus for detecting a substance in liquid that enables detection of a target substance in a liquid containing the target substance without immersing the sensor in the liquid, and that can provide highly accurate detection even when the amount of the liquid is small.

The sensor for detecting a substance in liquid according to a preferred embodiment of the present invention includes a base substrate and at least one SAW element disposed on one surface of the base substrate. The SAW element includes a surface acoustic wave substrate and at least one IDT electrode disposed on one surface of the surface acoustic wave substrate. A portion including the at least two IDT electrodes defines a sensing portion. The sensor also includes a resin layer covering one surface of the base substrate and the external surface of the at least one SAW element. The resin layer has an opening in which the sensing portion of the at least one SAW element is exposed at the one surface side of the base substrate. The sensing portion of at least one SAW element of the at least one SAW element is covered with a reaction film made of a material that binds to a detection target substance.

In a specific preferred embodiment of the sensor for detecting a substance in liquid according to the present invention, the SAW element is a resonator SAW filter.

In another specific preferred embodiment of the in-liquid substance detection sensor according to the present invention, the base substrate includes at least one recess, and the at least one SAW element is disposed in the at least one recess.

In still another preferred embodiment of the in-liquid substance detection sensor according to the present invention, the reaction film reacts with a specific protein.

In still another preferred embodiment of the in-liquid substance detection sensor according to the present invention, the resin layer on the base substrate includes a liquid-feed section defined by an opening provided in the upper surface thereof, and a flow channel defined by a groove that extends from the liquid-feed section to the sensing portion of the SAW element.

In still another preferred embodiment of the in-liquid substance detection sensor according to the present invention, the resin layer on one surface of the base substrate includes a liquid discharge section defined by an opening provided in the upper surface thereof, and a second flow channel defined by a groove that extends from the liquid discharge section to the sensing portion of the SAW element.

In still another preferred embodiment of the in-liquid substance detection sensor according to the present invention, the resin layer is made of a photosensitive resin.

In still another preferred embodiment of the in-liquid substance detection sensor according to the present invention, the photosensitive resin includes at least one selected from the group consisting of polyimide, polyethyl methacrylate, and epoxy resin.

The apparatus for detecting a substance in liquid according to another preferred embodiment of the present invention includes the sensor for detecting a substance in liquid according to any of the preferred embodiments of the present invention described above, an amplifier connected to the sensor for amplifying the output from the sensor, a frequency counter, and a controller.

The in-liquid substance detection sensor according to preferred embodiments of the present invention includes at least one SAW element disposed on one surface of a base substrate, and a resin layer covering the one surface of the base substrate and the external surface of the SAW element and including an opening in which the sensing portion of the SAW element is exposed. The surface of the sensing portion of at least one SAW element is covered with a reaction film made of a material that binds to a target substance. When dripping a liquid containing the target substance into the opening of the resin layer, the target substance is bound to the reaction film to vary the load on the sensing portion. Thus, the presence and/or concentration of the target substance is accurately detected. Since the measurement can be made by only dripping a liquid containing the target substance into the opening of the resin layer, the measurement does not require a large amount of liquid. In addition, since the SAW element is not immersed in the liquid, changes in measured value caused by immersing the SAW element do not occur.

Thus, preferred embodiments of the present invention achieve highly accurate measurements of a target substance in liquid even when the amount of the liquid is small.

If the SAW element is a resonator SAW filter, the loss is reduced.

If the SAW element is disposed in a recess provided in the base substrate, the presence of the recess enables a reduction in the thickness of the in-liquid substance detection sensor. In addition, by disposing the SAW element in the recess, the thickness of the resin layer provided on the one surface of the base substrate can be reduced.

If the reaction film reacts with a specific protein, the presence and/or concentration of the specific protein can be detected according to preferred embodiments of the present invention.

If the resin layer on the base substrate has a liquid-feed section defined by an opening provided in the upper surface of the resin layer and a flow channel defined by a groove that extends from the liquid-feed section to the sensing portion of the SAW element, a liquid containing a target substance can be fed from the liquid-feed section to deliver the liquid to the sensing portion of the SAW element through the groove or flow channel.

If the resin layer on the one surface of the base substrate includes a liquid discharge section defined by an opening provided in the upper surface of the resin layer and a second flow channel defined by a groove that extends from the liquid discharge section to the sensing portion of the SAW element, liquid can be discharged from the sensing portion to the liquid discharge section through the second flow channel. Thus, measurement can be continuously performed while liquid is continuously delivered to the sensing portion and discharged through the liquid discharge section.

If the resin layer is made of a photosensitive resin, the resin layer can be precisely patterned by photolithography.

If the photosensitive resin includes at least one selected from the group consisting of polyimide, polyethyl methacrylate, and epoxy resin, the resin layer having an opening can be precisely formed by photolithography.

An apparatus for detecting a substance in liquid according to preferred embodiments of the present invention includes a sensor for detecting a substance in liquid structured according to preferred embodiments of the present invention, an amplifier for amplifying the output from the sensor for detecting a substance in liquid, a frequency counter, and a controller. The frequency signals output according to the presence or concentration from the sensor are amplified by the amplifier and counted by the frequency counter. Since the apparatus uses the in-liquid substance detection sensor according to preferred embodiments of the present invention, the presence and/or concentration of the target substance can be detected with high accuracy.

Other features, elements, steps, characteristics and advantages of the present invention will become more apparent from the following detailed description of preferred embodiments of the present invention with reference to the attached drawings.

BRIEF DESCRIPTION OF THE DRAWINGS

FIG. 1A is a plan view; FIG. 1B is a fragmentary schematic side sectional view; and FIG. 1C is a fragmentary schematic front sectional view.

FIG. 4 is a process flow diagram of a method for manufacturing the in-liquid substance detection sensor of the first preferred embodiment of the present invention.

FIG. 12A is a plan view; FIG. 12B is a side sectional view; and FIG. 12C is a front sectional view.

DETAILED DESCRIPTION OF PREFERRED EMBODIMENTS

The present invention will be described in terms of specific preferred embodiments with reference to the drawings.

Figure 1A:
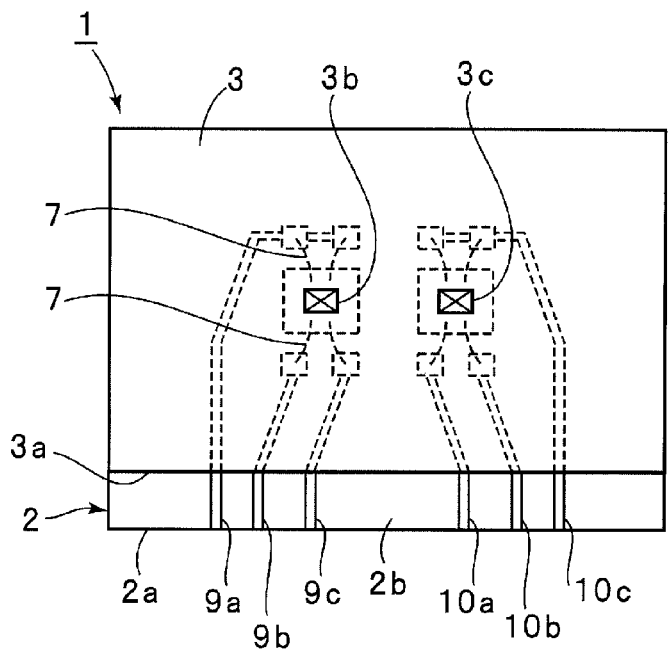
FIGS. 1A to 1C are representations of an in-liquid substance detection sensor according to a first preferred embodiment.
Figure 1B:
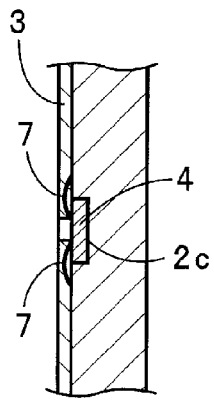
Figure 1C:
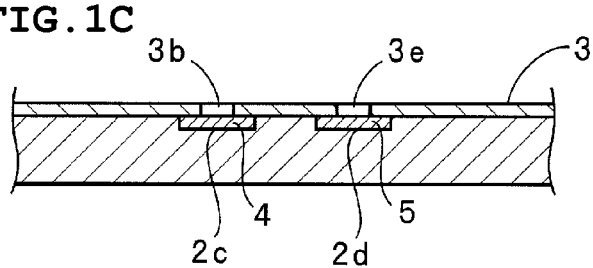

FIGS. 1A to 1C are representations of an in-liquid substance detection sensor according to a first preferred embodiment of the present invention: FIG. 1A is a plan view; FIGS. 1B and 1C are fragmentary front sectional and side sectional views.

Figure 2:
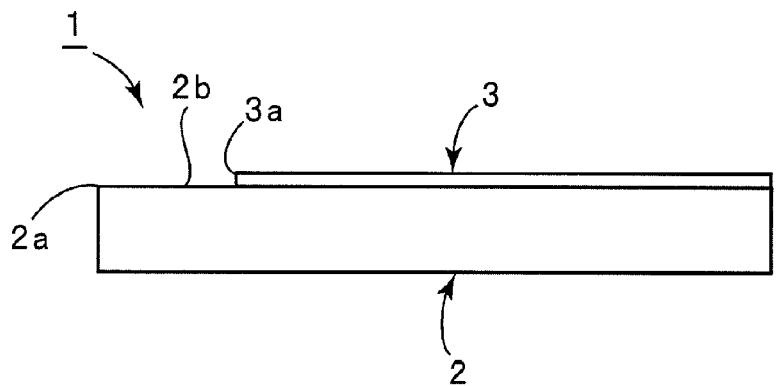
FIG. 2 is a side view of the in-liquid substance detection sensor according to the first preferred embodiment.

As shown in FIG. 1A, the in-liquid substance detection sensor 1 is preferably a substantially rectangular plate. The in-liquid substance detection sensor 1 includes a base substrate 2 and a resin layer 3 provided on the base substrate 2, as shown in the side view FIG. 2.

The base substrate 2 preferably has a substantially rectangular shape, and one end 2a protrudes from an end 3a of the resin layer 3. The portion of the base substrate protruding from the end 3a of the resin layer 3 is a protrusion 2b.

The base substrate 2 includes recesses 2c and 2d in the upper surface, as shown in FIG. 1C. The recesses 2c and 2d accommodate SAW elements 4 and 5, respectively, which are schematically shown in the figure. In other words, the base substrate 2 has a plurality of recesses 2c and 2d accommodating a plurality of SAW elements 4 and 5 in one surface.

The resin layer 3 includes openings 3b and 3c. The openings 3b and 3c have a diameter such that the sensing portions of the SAW elements 4 and 5 are exposed.

This structure will now be described more specifically with reference to FIGS. 3A and 3B.

Figure 3A:
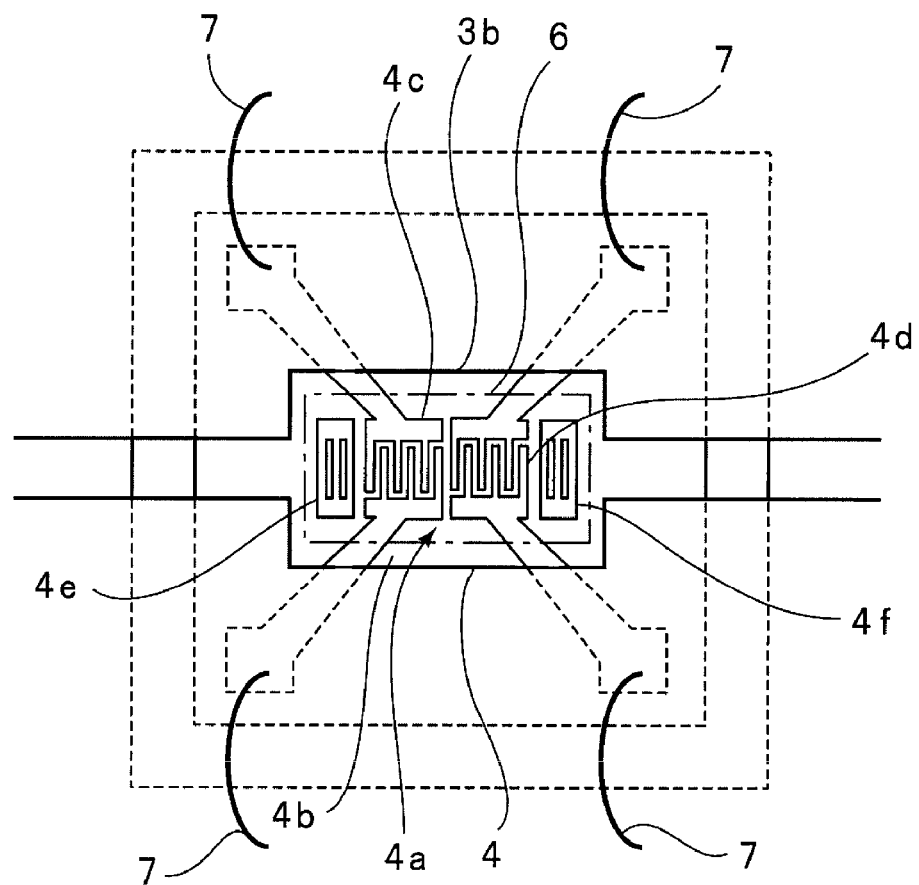
FIG. 3A is an enlarged schematic plan view of an opening and its vicinity of the in-liquid substance detection sensor of the first preferred embodiment.

FIG. 3A is an enlarged fragmentary schematic plan view of the portion at which the SAW element 4 is disposed. The opening 3b of the resin layer 3 preferably has a substantially rectangular shape and exposes the sensing portion 4a of the underlying SAW element 4. As shown in FIG. 3A, the SAW element 4 includes IDT electrodes 4c and 4d and reflectors 4e and 4f on a surface acoustic wave substrate 4b. The IDT electrodes 4c and 4d are arranged substantially in parallel in the direction in which surface acoustic waves propagate, and the reflectors 4e and 4f are arranged at both sides of the IDT electrodes 4c and 4d in the surface acoustic wave propagation direction.

The surface acoustic wave substrate 4b can be made of any suitable piezoelectric material. Exemplary piezoelectric materials include piezoelectric single crystals, such as lithium tantalate and lithium niobate, and piezoelectric ceramics, such as PZT ceramics. Lithium tantalate, lithium niobate, and PZT ceramics are particularly preferred because they stably propagate surface acoustic waves even in liquid.

The IDT electrodes 4c and 4d and the reflectors 4e and 4f can be made of any suitable metal or alloy, such as of aluminum or Ag.

The SAW elements 4 and 5 of the present preferred embodiment are resonator type surface acoustic wave filters as described above, and their losses are therefore low. However, the SAW element used in the present invention is not limited to the resonator type surface acoustic wave filter.

Figure 3B:
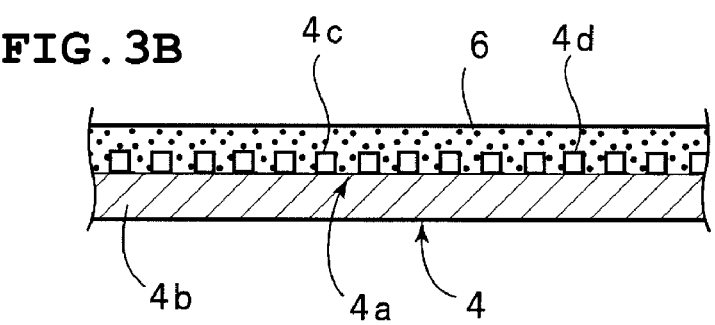
FIG. 3B is a fragmentary front sectional view showing the electrode structure and a reaction film of the sensing portion shown in FIG. 3A.

The sensing portion 4a at which the IDT electrodes 4c and 4d are disposed is covered with a reaction film 6, as shown in FIG. 3B. FIG. 3A indicates the location of the reaction film 6 by a dotted-chain line. The reaction film 6 in the present preferred embodiment is made of a material that binds to the target substance. This material is appropriately selected according to the type of target substance. For example, for the detection of a specific protein in a liquid, a material that binds to the protein is selected.

For example, cow serum albumin maybe detected as an example of the above protein. For this protein, the reaction film 6 may be made of, for example, N-2(aminoethyl)-3-aminopropyltrimethoxysilane [$(CH_3O)_3SiC_3H_6NHC_2H_4NH_2$].

The reaction film 6 may be made only of a material that binds to the target substance, or a compounded material including the target substance-binding material and another material acting as a matrix.

As shown in FIGS. 1A to 1C, the IDT electrodes 4c and 4d of the SAW element 4 in the present preferred embodiment are each electrically connected to an electrode disposed on the upper surface of the base substrate 2 with a bonding wire 7. The base substrate 2 includes wiring electrodes 9a to 9c on the surface that are electrically connected to a plurality of bonding wires 7. Each of the wiring electrodes 9a to 9c extend to an end 2a of the base substrate 2 on its upper surface.

For the other SAW element 5, the same reaction film is provided so as to cover the sensing portion, and the SAW element 5 is electrically connected to wiring electrodes 10a to 10c provided on the base substrate 2 with a plurality of bonding wires. The wiring electrodes 10a to 10c also extend to the end 2a of the base substrate 2.

In the in-liquid substance detection sensor 1, the wiring electrodes 9a to 9c and 10a to 10c for electrical connection extend to the protrusion 2b of the base substrate 2, so that electrical connection can be established between the wires 9a to 9C and 10a to 10c, and, for example, connection electrodes of a card insertion slot of a measuring apparatus when the protrusion 2b is inserted into the card insertion slot. With such a measuring apparatus, measurement results can be easily obtained only by feeding a liquid to the in-liquid substance detection sensor 1 and then inserting the protrusion 2b into the card insertion slot.

While the wiring electrodes 9a to 9c and 10a to 10c are preferably provided on the upper surface of the base substrate 2, they may be provided on the lower surface of the base substrate 2. In this instance, the wiring electrodes may be electrically connected to electrode pads connected to the bonding wires on the upper surface of the base substrate 2 with through hole electrodes. The arrangement of the wiring electrodes on the lower surface can prevent contact between the wiring electrode and liquid even if the liquid is accidentally spilled on the upper surface of the base substrate 2.

The resin layer 3 can be made of any suitable insulating resin. However, the openings 3b and 3c must be precisely formed in the resin layer 3 so as to expose the sensing portions, and it is preferable that the resin layer 3 be made of a photosensitive resin so that the openings 3b and 3c can be patterned by photolithography.

The resin material for the resin layer 3, however, is not particularly limited to photosensitive resin as long as it is curable. For example, a thermosetting resin, an instantaneously curable resin, or any other suitable resin can be used. In other words, the resin layer 3 can be formed of a variety of curable resins that can be applied onto the upper surface of the base substrate 2 and cured by applying heat or light or by being left to stand.

The openings 3b and 3c are preferably formed by photolithography if a photosensitive resin is used, but may be formed by other physical or chemical techniques, such as cutting, laser machining, blasting, and dissolving. In addition, the formation of the openings 3b and 3c may be performed before the resin layer 3 is completely cured.

The electrodes, such as the wiring electrodes 9a to 9c and 10a to 10c and the IDT electrode 4c and other IDT electrodes defining the sensing portions 4a of the SAW elements 4 and 5, may be covered with an insulating layer. By covering the electrodes with an insulating layer, short circuiting caused by liquid is prevented. Exemplary insulating materials for the insulating layer include, but are not limited to, SiN, $SiO_2$, $Ta_2O_5$, and $Al_2O_3$. In this instance, the thickness of the insulating layer is not particularly limited, but is preferably about 5 nm to about 1000 nm. The thickness in this range protects the electrodes of the SAW elements 4 and 5 without significantly affecting the characteristics of the SAW elements 4 and 5.

The bonding wires 7 are buried in the resin layer 3, as shown in FIG. 1B. However, the bonding wires 7 are not necessarily buried in the resin layer 3, and the resin layer 3 may include grooves in the lower surface in which the bonding wires 7 are embedded.

The resin layer 3 has a thickness so as to cover the bonding wires 7. Since the SAW elements 4 and 5 are disposed in the recesses 2c and 2d, the resin material for the resin layer 3 may have a relatively small thickness, and thus the surface of the resin layer 3 can be easily planarized.

In the present preferred embodiment, the electrical connection between the SAW elements 4 and 5 and the wiring electrodes 9a to 9c on the base substrate is made with a plurality of bonding wires 7. As an alternative to the bonding wires 7, TAB (Tape Automated Bonding) or any other electroconductive connection member may be used.

The process for manufacturing the in-liquid substance detection sensor 1 is not particularly limited, but, for example, the in-liquid substance detection sensor 1 may be manufactured in a process including Steps S1 to S6 shown in FIG. 4. In this process, the SAW elements 4 and 5 are disposed and fixed in the recesses 2c and 2d of the base substrate 2 in Step S1. Then, in Step S2, the SAW elements 4 and 5 are electrically connected to the wiring electrodes on the base substrate with the bonding wires. Subsequently, masks are placed over the sensing portions of the SAW elements 4 and 5 in Step S3. The reaction film can be fixed to either of the sensing portions of the SAW elements 4 and 5 in advance, or just before the time of measurement after assembling.

Then, a curable resin is applied on the base substrate 2 in Step S4, and is cured in Step S5. The resin layer 3 is thus formed. Then, in Step S6, the masks covering the sensing portions are removed. Thus, the openings 3b and 3c are formed and the in-liquid substance detection sensor 1 is completed.

The operation of the in-liquid substance detection sensor 1 will now be described.

For detecting a substance in liquid, a liquid containing a target substance is fed into the openings 3b and 3c, which define liquid-feed openings. The liquid is fed by injecting or dripping the liquid into the openings 3b and 3c using a syringe or a pipette. Thus, the openings 3b and 3c are filled with the liquid. The liquid comes into contact with the sensing portions of the SAW elements 4 and 5 exposed in the openings 3b and 3c. For example, if the reaction film 6 is fixed to the sensing portion of the SAW element 4 and the liquid contains a target substance, the target substance is bound to the reaction film 6, and consequently, the load placed on the sensing portion of the SAW element 4 is varied. Accordingly, the load on the SAW element 5, which does not have the reaction film 6 and which defines a reference, and the load on the SAW element 4 to which the reaction film 6 is fixed varies. The outputs of the SAW elements 4 and 5 are thus changed so that the presence or absence of the target substance or the concentration of the target substance can be measured.

Figure 6:
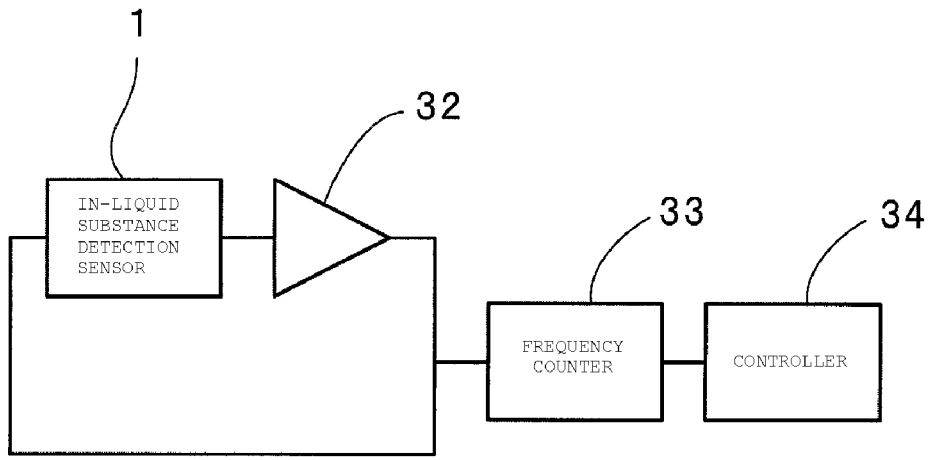
FIG. 6 is a block diagram of an in-liquid substance detection apparatus including the in-liquid substance detection sensor of the first preferred embodiment of the present invention.

The in-liquid substance detection apparatus including the in-liquid substance detection sensor 1 of the present preferred embodiment is not particularly limited, but, for example, an apparatus as shown in FIG. 6 may be used. In the apparatus, an amplifier 32 may be connected to the output end of the in-liquid substance detection sensor 1 and the output of the amplifier 32 may be connected to the input end of the in-liquid substance detection sensor 1. In addition, the output end of the amplifier 32 is connected to a frequency counter 33 and the output end of the frequency counter 33 is connected to a controller 24. The controller 34 determines the measurement results according to the signals from the frequency counter 33.

Figure 5A:
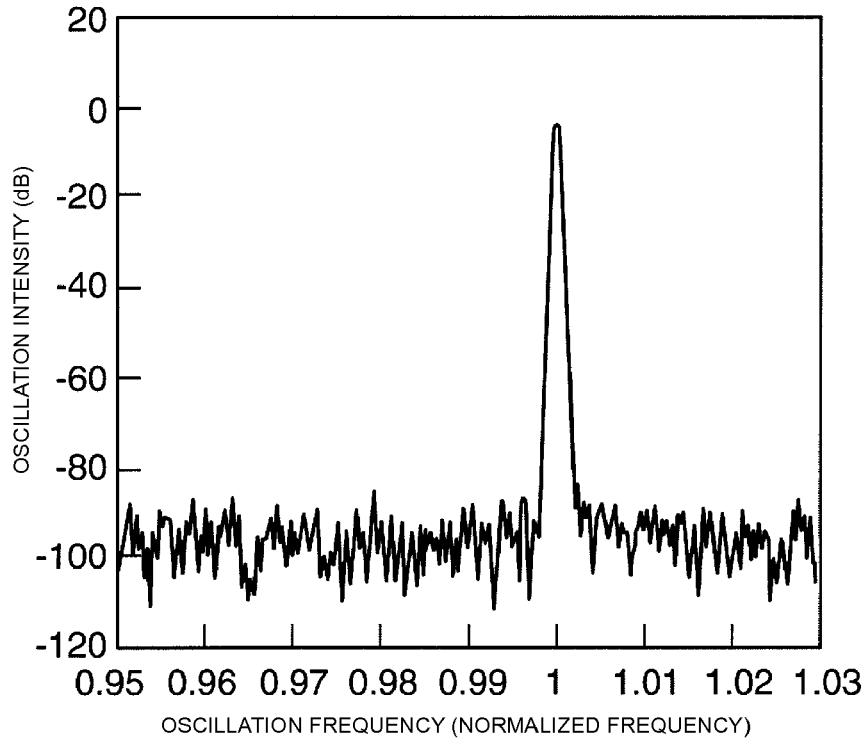
FIG. 5A is a graph of an output measured using the in-liquid substance detection sensor of the first preferred embodiment.

FIG. 5A is a graph of output signals as the results of measurement of a liquid, physiological saline containing cow serum albumin, using the reaction film 6 made of the above mentioned material capable of binding cow serum albumin.

As shown in FIG. 5A, oscillation intensity for normalized oscillation frequency (frequency/SAW oscillation frequency) is very high because of the presence of cow serum albumin, and accordingly, the presence of cow serum albumin can be accurately detected.

Figure 5B:
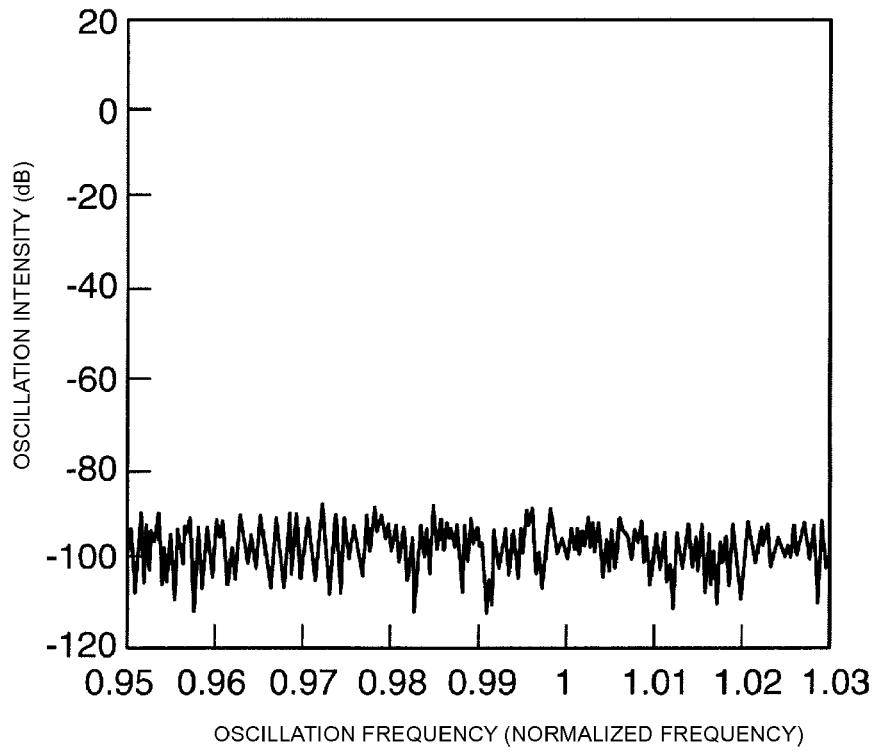
FIG. 5B is a graph of an output measured using a known in-liquid substance detection sensor.

FIG. 5B shows the output signals of the measurement in which a known in-liquid substance detection sensor including an SAW element having a similar structure as the SAW element 4 was immersed in the physiological saline containing cow serum albumin. As shown in FIG. 5B, the cow serum albumin was not detected. This may be because the measurement sensitivity is not sufficient.

Figure 7:
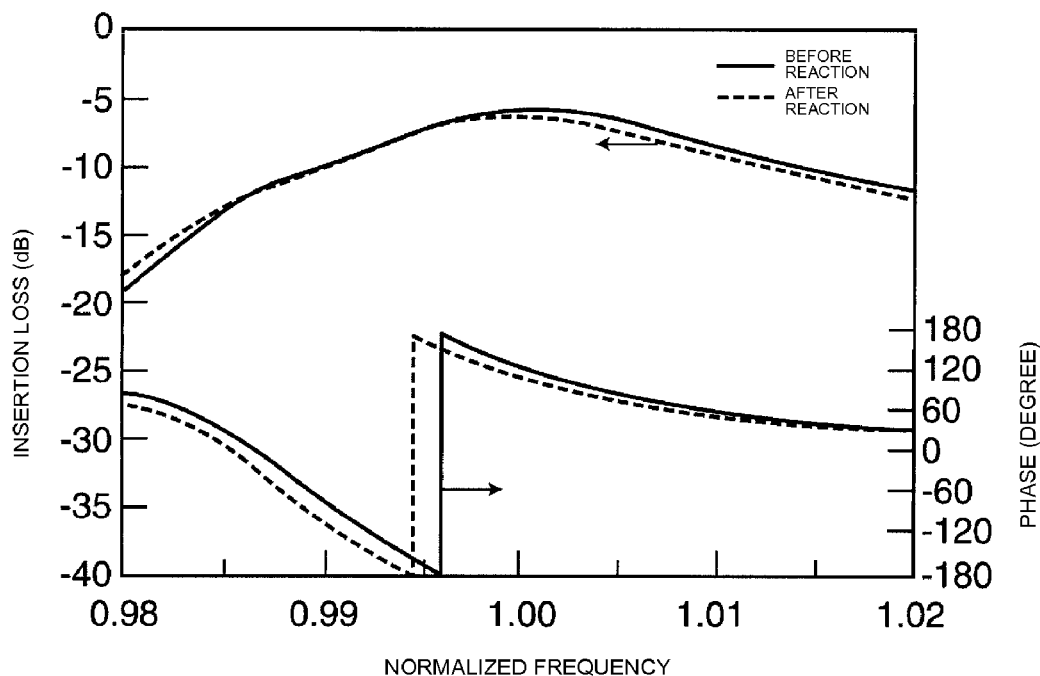
FIG. 7 is a graph showing the results of the measurement of a physiological saline containing cow serum albumin with the in-liquid substance detection sensor of the first embodiment of the present invention.

FIG. 7 is a graph of the results obtained from the measurement of physiological saline containing cow serum albumin with the in-liquid substance detection sensor 1 of the above preferred embodiment. In FIG. 7, the solid line indicates the results of measurement before reaction, that is, measurement of physiological saline not containing cow serum albumin, and the dashed line indicates the results of measurement of physiological saline containing 5 μg/ml of cow serum albumin. FIG. 7 shows the characteristic of insertion loss vs. frequency and the characteristic of phase vs. frequency. The characteristics of the SAW elements 4 and 5 are notably changed when the physiological saline containing cow serum albumin is fed. The characteristics shown here are averages of the characteristics of the SAW elements 4 and 5.

Figure 8:
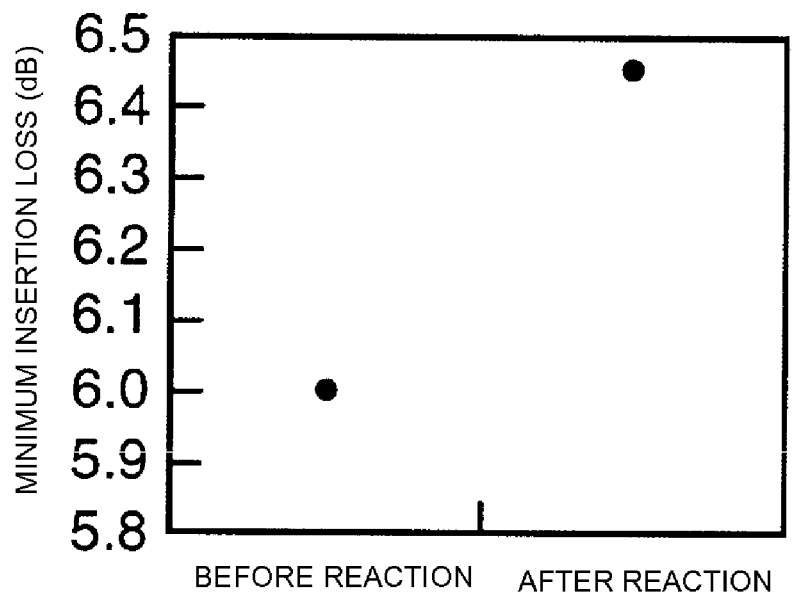
FIG. 8 is a representation of the difference between the minimum insertion losses before and after reaction derived from the measurement results shown in FIG. 7.
Figure 9:
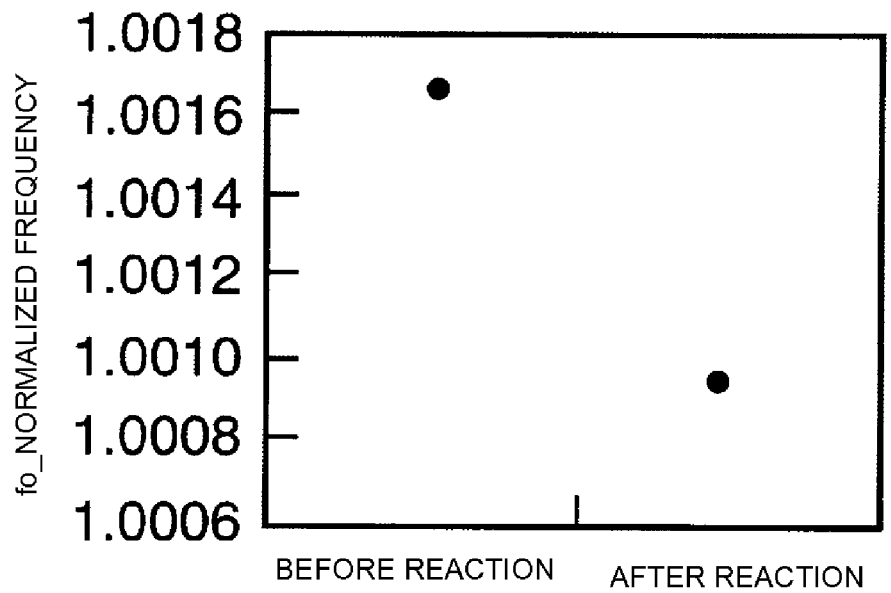
FIG. 9 is a representation of the normalized frequencies for the minimum insertion losses before and after reaction derived from the measurement results shown in FIG. 7.
Figure 10:
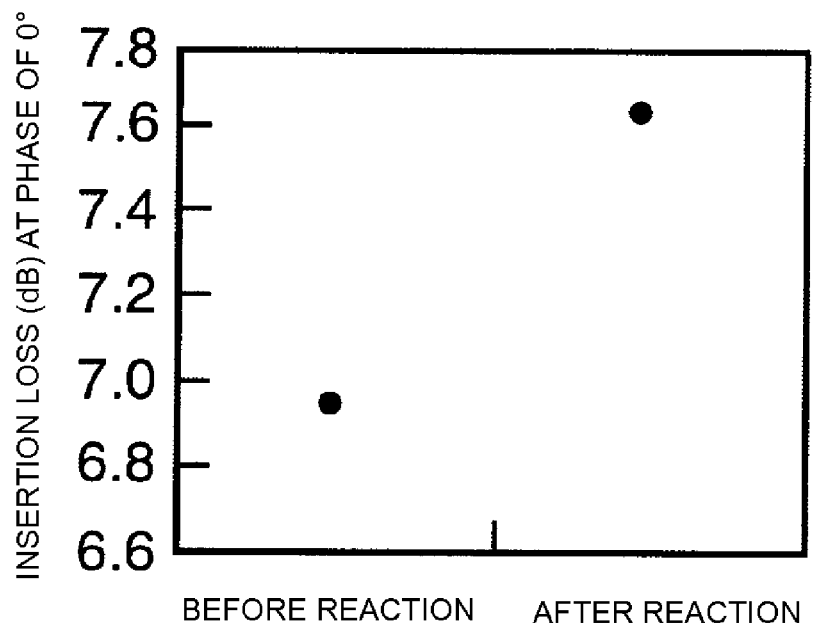
FIG. 10 is a representation of the difference between the insertion losses at a phase of 0° before and after reaction derived from the measurement results shown in FIG. 7.
Figure 11:
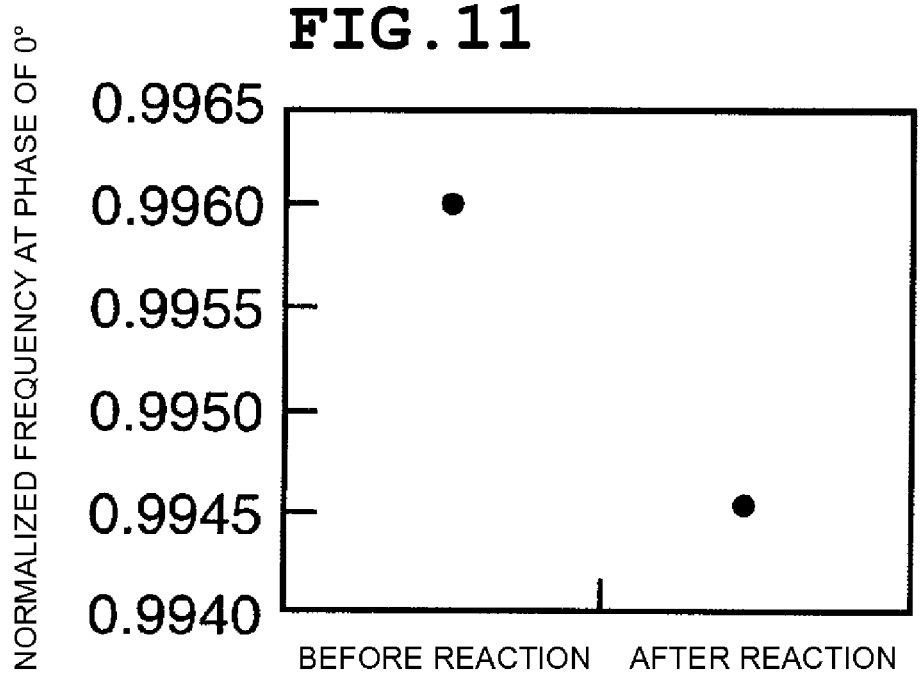
FIG. 11 is a representation of the difference between the normalized frequencies at a phase of 0° before and after reaction derived from the measurement results shown in FIG. 7.

For ease of comparison, the results shown in FIG. 7 are separated into the results before reaction and the results after reaction in FIGS. 8 to 11. FIG. 8 shows minimum insertion losses; FIG. 9 shows normalized frequencies at which the minimum insertion losses notably change; FIG. 10 shows insertion losses at a phase of 0°; and FIG. 11 shows normalized frequencies at a phase of 0°.

As shown in FIGS. 8 to 11, the minimum insertion loss, the normalized frequency at which the insertion loss notably changes, and the insertion loss and normalized frequency at a phase of 0° are significantly changed before and after reaction. This shows that by detecting these changes, the presence or absence of cow serum albumin can be detected with high accuracy.

Figure 12A:
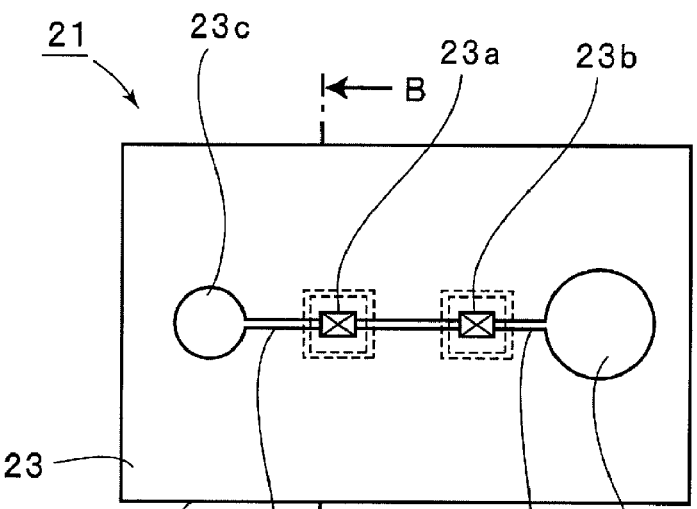
FIGS. 12A to 12C are representations of an in-liquid substance detection sensor according to a second preferred embodiment of the present invention.
Figure 12B:
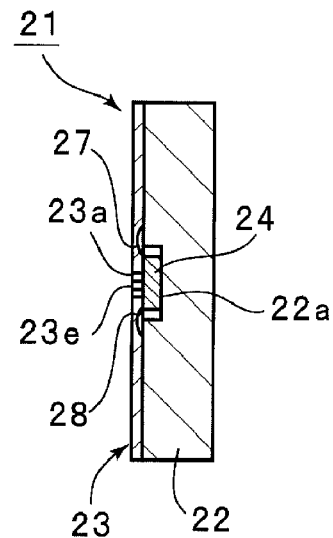
Figure 12C:
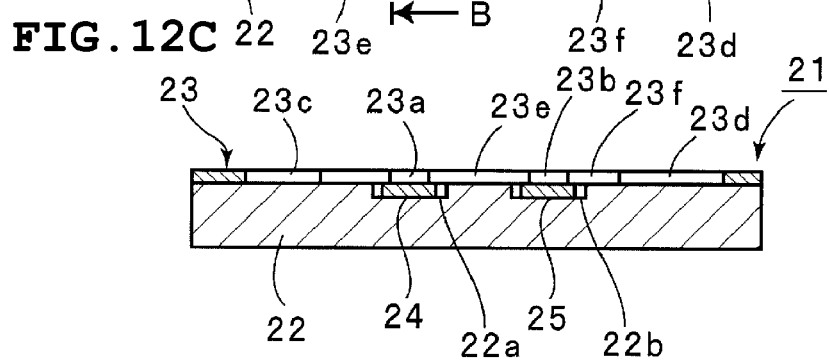

FIGS. 12A to 12C are representations of an in-liquid substance detection sensor according to a second preferred embodiment: FIG. 12A is a plan view; FIG. 12B is a sectional view taken along line B-B; and FIG. 12C is a front sectional view.

In the in-liquid substance detection sensor 21, a resin layer 23 is provided on the base substrate 22. The base substrate 22 includes recesses 22a and 22b in the upper surface. The recesses 22a and 22b accommodate a plurality of SAW elements 24 and 25, respectively.

The SAW element 24 is electrically connected to electrodes (not shown) on the base substrate 22 with bonding wires 27 and 28, as shown in FIG. 12B. The structure of the in-liquid substance detection sensor 21 is the same as the structure of the in-liquid substance detection sensor 1 of the first preferred embodiment, except that the base substrate 22 has the same size as the resin layer 23.

One of the unique features of the present preferred embodiment is that the resin layer 23 includes not only openings 23a and 23b, but also a liquid-feed opening 23c, a liquid discharge opening 23d, a first flow channel 23e, and a second flow channel 23f. The other structure of the in-liquid substance detection sensor 21 is preferably substantially the same as the in-liquid substance detection sensor 1 of the first preferred embodiment.

Figure 13:
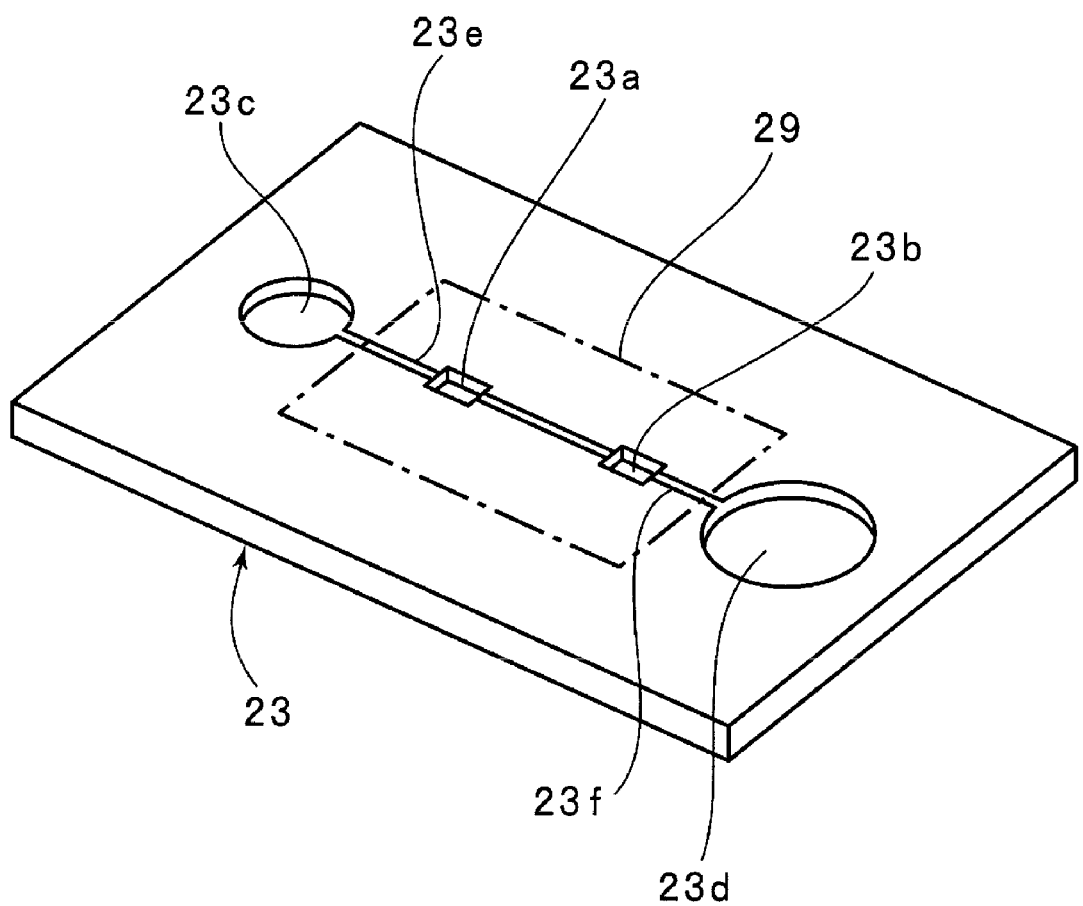
FIG. 13 is a perspective view of the structure of a resin layer of the in-liquid substance detection sensor according to the second preferred embodiment of the present invention.

As shown in an enlarged perspective view FIG. 13, the circular liquid-feed opening 23c defining a liquid-feed section communicates with the opening 23a through the first flow channel 23e in the resin layer 23. The first flow channel 23e preferably has a width of about 10 μm to about 100 μm, for example. In the present preferred embodiment, a liquid containing a target substance is fed into the liquid-feed opening 23c. As a result, the liquid is delivered to the opening 23a midway along the first flow channel 23e. The liquid comes into contact with the sensing portion of the SAW element 24 in the opening 23a. The first flow channel 23e extends to the opening 23b. Therefore, the liquid flows to the opening 23b, and thus, comes into contact with the sensing portion of the SAW element 25 in the opening 23b. Then, the liquid flows into the liquid discharge opening 23d defining a liquid discharge section through the second flow channel 23f.

The liquid discharged from the liquid discharge opening 23d can be removed with a micropipette or a tube. In some cases, the liquid-feed opening 23c may be connected to the tip of a pipette or a tube and the tip of a tube or the tip of a syringe placed in the liquid discharge opening 23d, so that the liquid can be continuously fed from the liquid-feed opening 23c and discharged from the liquid discharge opening 23d.

In this instance, pressure for delivering the liquid may be applied from the liquid-feed opening 23c and/or drawn from the liquid discharge opening 23d to smoothly deliver the liquid to the openings 23a and 23b. Thus, continuous measurement can be achieved using the SAW elements 24 and 25.

Figure 14:
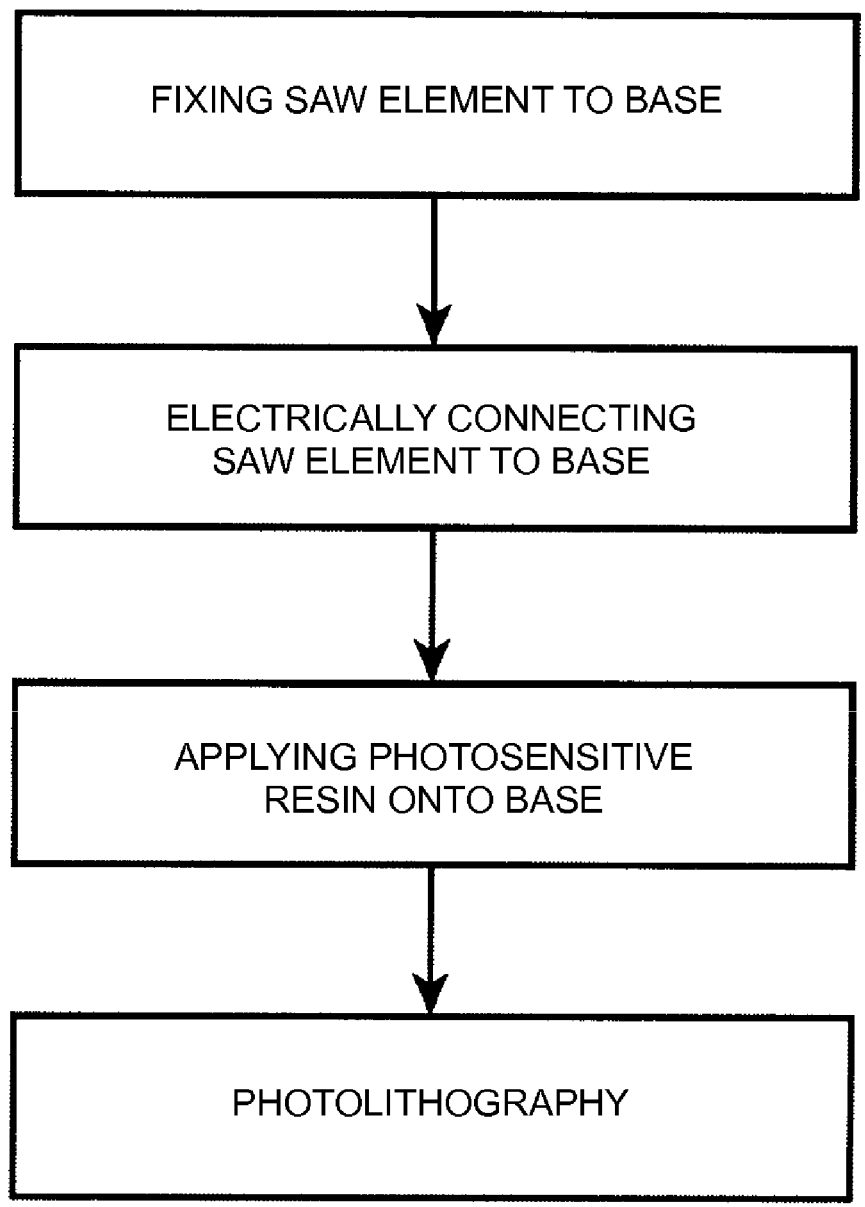
FIG. 14 is a process flow diagram of a method for manufacturing the in-liquid substance detection sensor according to the second preferred embodiment of the present invention.

FIG. 14 is a process flow diagram of a method for manufacturing the in-liquid substance detection sensor 21 of the second preferred embodiment. For the manufacture of the in-liquid substance detection sensor 21, first, the base substrate 22 is prepared. Then, the SAW elements 24 and 25 are disposed in the recesses 22a and 22b in the upper surface of the base substrate 22, respectively, and are electrically connected to electrodes (not shown) on the base substrate with bonding wires. Subsequently, a photosensitive resin is applied on the upper surface of the base substrate 22 and patterned by photolithography to form the resin layer 23 having the openings 23a and 23b, the liquid-feed opening 23c, the liquid discharge opening 23d, the first flow channel 23e, and the second flow channel 23f.

The resin layer 23 is not necessarily formed by photolithography using a photosensitive resin, but may be formed by other techniques. However, photolithography facilitates the formation of fine shapes, such as the flow channels 23e and 23f, with high precision. It is therefore preferable that the resin layer 23 be formed by photolithography using a photosensitive resin.

The SAW elements 4 and 5 can be defined by other types of surface acoustic wave elements, such as transversal surface acoustic wave filters. If a resonator surface acoustic wave filter is used, it may be a longitudinally coupled type or a transversely coupled type. The photosensitive resin, if used, may be of a negative type or a positive type.

The photosensitive resin is not particularly limited, but, for example, may be a resin primarily including polyimide resin, polymethyl methacrylate resin, or epoxy resin to form a resin layer 23 with a high shape precision.

Since photolithography facilitates the formation of fine flow channels with high precision as described above, the flow rate of liquid flowing through the flow channel 23e and 23f and the openings 23a and 23b can be accurately controlled, and consequently, the detection accuracy can be effectively improved. While the flow of the liquid through the fine flow channels 24e and 24f is produced by capillary action, a liquid supply delivering apparatus, such as a pump, may be used in some cases.

When only the presence or absence of the target substance is required, and not its concentration, the flow channels 24e and 24f may not necessarily be provided, and only the sensing portions my be exposed in the openings as in the first preferred embodiment.

In order to prevent the liquid from leaking from the flow channels 23e and 23f and the openings 23a and 23b, a covering member 29 may be provided in the region designated by the dotted chain line in FIG. 13. The covering member 29 may be, for example, a synthetic resin film.

Figure 15:
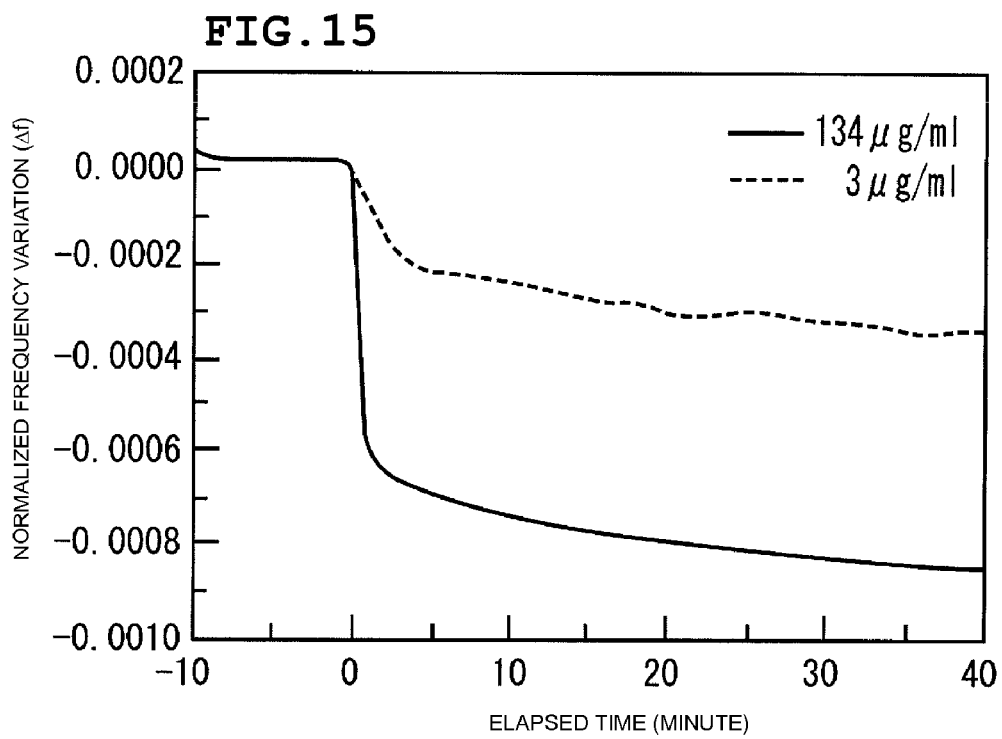
FIG. 15 is a graph of the results of measurements using the in-liquid substance detection sensor of the second preferred embodiment of the present invention.
Figure 16:
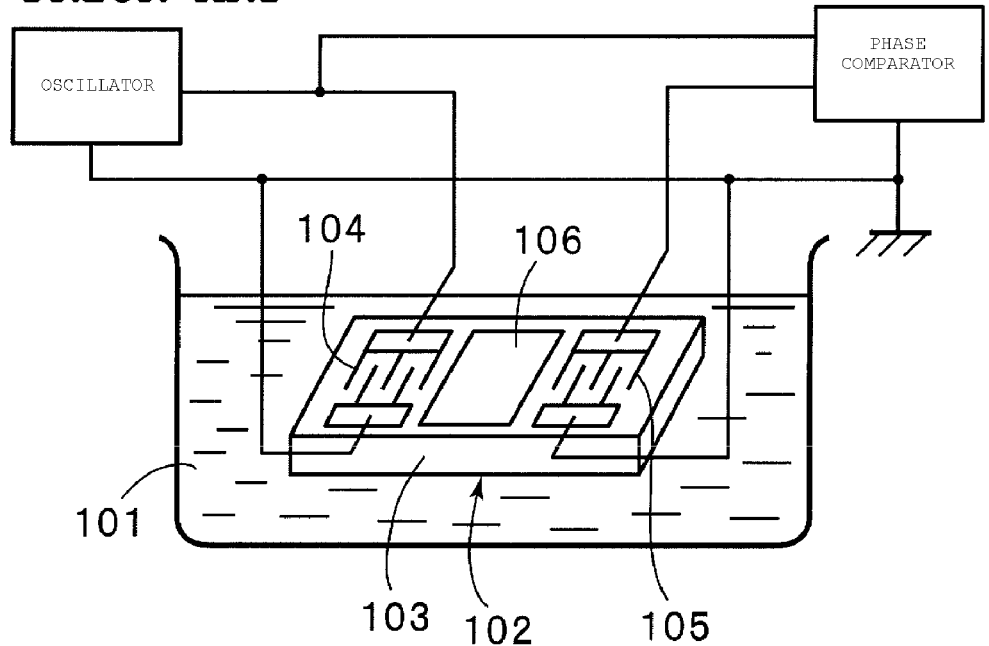
FIG. 16 is a schematic representation of a known in-liquid substance detection sensor.

FIG. 15 is a graph of the results of measurement using the in-liquid substance detection sensor of the second preferred embodiment. In FIG. 15, the solid line indicates the measurement results of a solution of about 134 μg/ml cow serum albumin in physiological saline, and the dashed line indicates the measurement results of about 3 μg/ml cow serum albumin. FIG. 15 clearly shows that a change in cow serum albumin concentration can be accurately detected from the variation in normalized frequency.

While the above described preferred embodiments preferably use two SAW elements, only one SAW element may be used. The present invention does not necessarily require the use of a plurality of SAW elements, but does require the use of a plurality of IDTs (sensing portion).

While the above-described preferred embodiments use two SAW elements and one of which is covered with a reaction film, three or more SAW elements may be used.

When three SAW elements are used, the following structure may be provided, for example. First and second SAW elements of the three SAW elements can be covered with the reaction film and a third SAW element dos not include a reaction film. In this instance, the third SAW element defines a reference SAW element. A liquid is fed to the exposed first to third SAW elements and the frequencies are measured. A first frequency variation being the difference between the frequencies measured at the first SAW element and at the third SAW element and a second frequency variation being the difference between the frequencies measured at the second SAW element and at the third SAW element are obtained, and the first and second variations are averaged. Thus, the accuracy of measurement of a target substance based on the variation in frequency can be increased.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A sensor for detecting a substance in liquid, comprising:
   a base substrate;
   at least one SAW element disposed on one surface of the base substrate, including a surface acoustic wave substrate and at least one IDT electrode disposed on one surface of the surface acoustic wave substrate, a portion of the at least one SAW element including said at least one IDT electrode defining a sensing portion;
   a resin layer arranged to cover the one surface of the base substrate and an external surface of the at least one SAW element, the resin layer having an opening in which the sensing portion of the at least one SAW element is exposed at the one surface side of the base substrate; and
   a reaction film arranged to cover the sensing portion of said at least one SAW element, the reaction film being made of a material that binds to a detection target substance; wherein
   the base substrate includes at least one recess and said at least one SAW element is disposed in said at least one recess.

2. The sensor for detecting a substance in liquid according to claim 1, wherein the SAW element is a resonator SAW filter.

3. The sensor for detecting a substance in liquid according to claim 1, wherein the reaction film reacts with a specific protein.

4. The sensor for detecting a substance in liquid according to claim 1, wherein the resin layer includes a liquid-feed section defined by an opening provided in an upper surface thereof, and a flow channel defined by a groove that extends from the liquid-feed section to the sensing portion of the SAW element.

5. The sensor for detecting a substance in liquid according to claim 4, wherein the resin layer further includes a liquid discharge section defined by an opening provided in the upper surface thereof, and a second flow channel defined by a groove that extends from the liquid discharge section to the sensing portion of the SAW element.

6. The sensor for detecting a substance in liquid according to claim 1, wherein the resin layer is made of a photosensitive resin.

7. The sensor for detecting a substance in liquid according to claim 6, wherein the photosensitive resin includes at least one selected from the group consisting of polyimide, polyethyl methacrylate, and epoxy resin.

8. An apparatus for detecting a substance in liquid comprising:
   a sensor arranged to detect a substance in liquid according to claim 1;
   an amplifier connected to the sensor and arranged to amplify the output from the sensor so as to detect a substance in liquid;
   a frequency counter; and
   a controller.

* * * * *